US012788490B2

(12) United States Patent
Coronel et al.

(10) Patent No.: US 12,788,490 B2
(45) Date of Patent: Nov. 10, 2026

(54) VENTRICULAR TACHYCARDIA ABLATION SITE IDENTIFICATION

(71) Applicants: THE JOHNS HOPKINS UNIVERSITY, Baltimore, MD (US); STICHTING AMSTERDAM UMC, Amsterdam (NL)

(72) Inventors: Ruben Coronel, Abcoude (NL); Pouya Jelvehgaran, Amsterdam (NL); Ryan P. O'Hara, Baltimore, MD (US); Natalia A. Trayanova, Baltimore, MD (US)

(73) Assignees: THE JOHNS HOPKINS UNIVERSITY, Baltimore, MD (US); STICHTING AMSTERDAM UMC, Amsterdam (NL)

( * ) Notice: Subject to any disclaimer, the term of this patent is extended or adjusted under 35 U.S.C. 154(b) by 309 days.

(21) Appl. No.: 18/294,762

(22) PCT Filed: Aug. 4, 2022

(86) PCT No.: PCT/US2022/039382

§ 371 (c)(1),
(2) Date: Feb. 2, 2024

(87) PCT Pub. No.: WO2023/018593

PCT Pub. Date: Feb. 16, 2023

(65) Prior Publication Data

US 2025/0221771 A1 Jul. 10, 2025

Related U.S. Application Data

(60) Provisional application No. 63/231,466, filed on Aug. 10, 2021.

(51) Int. Cl.
*A61B 34/10* (2016.01)
*A61B 18/00* (2006.01)
*A61B 18/14* (2006.01)

(52) U.S. Cl.
CPC .......... *A61B 34/10* (2016.02); *A61B 18/1492* (2013.01); *A61B 2018/00351* (2013.01);
(Continued)

(58) Field of Classification Search
CPC ................ A61B 34/10; A61B 18/1492; A61B 2018/00351; A61B 2018/00577;
(Continued)

(56) References Cited

U.S. PATENT DOCUMENTS

| | | | |
|---|---|---|---|
| 2019/0197199 | A9 | 6/2019 | Mansi et al. |
| 2021/0085399 | A1 | 3/2021 | Trayanova et al. |

OTHER PUBLICATIONS

Alturki, Ahmed et al. "Anti-arrhythmic drug therapy in implantable cardioverter-defibrillator recipients." Pharmacological research 143 (2019): 133-142.

(Continued)

*Primary Examiner* — Beverly M Flanagan
(74) *Attorney, Agent, or Firm* — MH2 Technology Law Group LLP

(57) ABSTRACT

A system for, and method of, identifying an ablation site are presented. The techniques of the method and implemented by the system may include: generating a model of at least one ventricle of a patient; simulating pacing, in the model, where the simulating pacing induces a simulated premature heartbeat in the model; recording an activation time and a repolarization time resulting from the simulating pacing at each of multiple nodes in the model; determining, based on the multiple activation times and repolarization times, a reentry susceptibility quantification at each of multiple nodes in the model; identifying a candidate ablation site based on the multiple reentry susceptibility quantifications;
(Continued)

simulating, in the model, an ablation at the candidate ablation site; and determining, using the model, that the simulating the ablation prevents a simulated pacing from inducing simulated reentrant ventricular tachycardia.

20 Claims, 9 Drawing Sheets

(52) U.S. Cl.
CPC ............... *A61B 2018/00577* (2013.01); *A61B 2018/00642* (2013.01); *A61B 2018/00773* (2013.01); *A61B 2034/104* (2016.02); *A61B 2034/105* (2016.02)

(58) Field of Classification Search
CPC ........... A61B 2018/00642; A61B 2018/00733; A61B 2034/104; A61B 2034/105; A61B 2576/023; A61B 5/0044; A61B 5/055; A61B 5/362; A61B 5/349; G16H 50/50
USPC ............................................................ 606/41
See application file for complete search history.

(56) References Cited

OTHER PUBLICATIONS

Arevalo, Hermenegildj et al. "Arrhythmia risk stratification of patients after myocardial infarction using personalized heart models." Nature communications 7.1 (2016): 11437.
Barr, Roger C. et al. "Relating epicardial to body surface potential distributions by means of transfer coefficients based on geometry measurements." IEEE Transactions on biomedical engineering 1 (1977): 1-11.
Bayer, Jason D. et al. "A novel rule-based algorithm for assigning myocardial fiber orientation to computational heart models." Annals of biomedical engineering 40 (2012): 2243-2254.
Callans, David J. et al. "Repolarization heterogeneity in human post-infarct ventricular tachycardia." Clinical Electrophysiology 8.6 (2022): 713-718.
Carbucicchio, C. et al. "STRA-MI-VT (STereotactic RadioAblation by Multimodal Imaging for Ventricular Tachycardia): rationale and design of an Italian experimental prospective study." Journal of Interventional Cardiac Electrophysiology 61 (2021): 583-593.
Cluitmans, Matthijs JM et al. "In vivo validation of electrocardiogramaging." JACC: Clinical Electrophysiology 3.3 (2017): 232-242.
Connolly, Stuart J. et al. "Meta-analysis of the implantable cardioverter defibrillator secondary prevention trials." European heart journal 21.24 (2000): 2071-2078.
Coronel, Ruben et al. "Anti-or profibrillatory effects of Na+ channel blockade depend on the site of application relative to gradients in repolarization." Frontiers in Physiology 1 (2010): 1741.
Coronel, Ruben et al. "Dispersion of repolarization and arrhythmogenesis." Heart Rhythm 6.4 (2009): 537-543.
De Bakker, J. M. et al. "Slow conduction in the infarcted human heart.'Zigzag'course of activation." Circulation 88.3 (1993): 915-926.
Deng, Dongdong et al. "Sensitivity of ablation targets prediction to electrophysiological parameter variability in image-based computational models of ventricular tachycardia in post-infarction patients." Frontiers in Physiology 10 (2019): 628.
Dinov, Borislav et al. "Outcomes in catheter ablation of ventricular tachycardia in dilated nonischemic cardiomyopathy compared with ischemic cardiomyopathy: results from the Prospective Heart Centre of Leipzig VT (HELP-VT) Study." Circulation 129.7 (2014): 728-736.
Hill, Yolanda R. et al. "Investigating a novel activation-repolarisation time metric to predict localised vulnerability to reentry using computational modelling." PLoS One 11.3 (2016): e0149342.
Hongo, Richard H. "Catheter Ablation of Scar-mediated Ventricular Tachycardia: Are Substrate-based Approaches Replacing Mapping?." The Journal of Innovations in Cardiac Rhythm Management 10.6 (2019): 3707.
Huiskamp, Geertjan et al. "Tailored versus realistic geometry in the inverse problem of electrocardiography." IEEE Transactions on Biomedical Engineering 36.8 (1989): 827-835.
Ilg, Karl et al. "Assessment of radiofrequency ablation lesions by CMR imaging after ablation of idiopathic ventricular arrhythmias." JACC: Cardiovascular Imaging 3.3 (2010): 278-285.
Janssen, Arno M. et al. "Assessment of the equivalent dipole layer source model in the reconstruction of cardiac activation times on the basis of BSPMs produced by an anisotropic model of the heart." Medical & biological engineering & computing 56 (2018): 1013-1025.
Jelvehgaran, Pouya et al. "Computational re-entry vulnerability index mapping to guide ablation in patients with postmyocardial infarction ventricular tachycardia." Clinical Electrophysiology 9.3 (2023): 301-310.
Koplan, Bruce A. et al. "Ventricular tachycardia and sudden cardiac death." Mayo clinic proceedings. vol. 84. No. 3. Elsevier, 2009.
McAnulty J. et al. Antiarrhythmics versus Implantable Defibrillators (AVID) Investigators. "A comparison of antiarrhythmic-drug therapy with implantable defibrillators in patients resuscitated from near-fatal ventricular arrhythmias." New England Journal of Medicine 337.22 (1997): 1576-1584.
Moss, Arthur J. et al. "Prophylactic implantation of a defibrillator in patients with myocardial infarction and reduced ejection fraction." New England Journal of Medicine 346.12 (2002): 877-883.
Orini, Michele et al. "Sequential Electro-Anatomical Mapping Methodology and Preliminary Results for Reentry Vulnerability Index Estimation." 2018 Computing in Cardiology Conference (CinC). vol. 45. IEEE, 2018.
Peyre, Gabriel et al. "Geodesic remeshing using front propagation." International Journal of Computer Vision 69 (2006): 145-156.
Prakosa, A. et al. "Methodology for image-based reconstruction of ventricular geometry for patient-specific modeling of cardiac electrophysiology." Progress in biophysics and molecular biology 115.2-3 (2014): 226-234.
Prakosa, A. et al. "Personalized virtual-heart technology for guiding the ablation of infarct-related ventricular tachycardia." Nature biomedical engineering 2.10 (2018): 732-740.
Prassl, Anton J. et al. "Automatically generated, anatomically accurate meshes for cardiac electrophysiology problems." IEEE Transactions on Biomedical Engineering 56.5 (2009): 1318-1330.
Ramanathan, Charulatha et al. "Noninvasive electrocardiogramaging (ECGI): application of the generalized minimal residual (GMRes) method." Annals of biomedical engineering 31 (2003): 981-994.
Robinson, Clifford G. et al. "Phase I/II trial of electrophysiology-guided noninvasive cardiac radioablation for ventricular tachycardia." Circulation 139.3 (2019): 313-321.
Rudy, Yoram. "Noninvasive electrocardiogramaging in humans." Journal of Electrocardiology 38.4S (2005): 138.
Santangeli, Pasquale et al. "Substrate mapping for unstable ventricular tachycardia." Heart Rhythm 13.2 (2016): 569-583.
Sasano, Tetsuo et al. "Molecular ablation of ventricular tachycardia after myocardial infarction." Nature medicine 12.11 (2006): 1256-1258.
Shivkumar, Kalyanam. "Catheter ablation of ventricular arrhythmias." New England Journal of Medicine 380.16 (2019): 1555-1564.
Shun-Shin, Matthew J. et al. "Implantable cardioverter defibrillators for primary prevention of death in left ventricular dysfunction with and without ischaemic heart disease: a meta-analysis of 8567 patients in the 11 trials." European heart journal 38.22 (2017): 1738-1746.
Stevenson, William G. et al. "Identification of reentry circuit sites during catheter mapping and radiofrequency ablation of ventricular tachycardia late after myocardial infarction." Circulation 88.4 (1993): 1647-1670.

(56) References Cited

OTHER PUBLICATIONS

Stubhan, Miriam et al. "Evaluation of cardiovascular and ECG parameters in the normal, freely moving Göttingen Minipig." Journal of Pharmacological and Toxicological Methods 57.3 (2008): 202-211.

Talib, Ahmed Karim et al. "Catheter ablation for Brugada syndrome." Korean circulation journal 50.4 (2020): 289-301.

Tung, Roderick et al. "Freedom from recurrent ventricular tachycardia after catheter ablation is associated with improved survival in patients with structural heart disease: an International VT Ablation Center Collaborative Group study." Heart rhythm 12.9 (2015): 1997-2007.

Van Dam, Peter M. et al. "Application of the fastest route algorithm in the interactive simulation of the effect of local ischemia on the ECG." Medical & biological engineering & computing 47 (2009): 11-20.

Van Der Ree, Martijn H. et al. "Cardiac radioablation—A systematic review." Heart rhythm 17.8 (2020): 1381-1392.

Van Der Waal, Jeanne et al. "In silico validation of electrocardiogramaging to reconstruct the endocardial and epicardial repolarization pattern using the equivalent dipole layer source model." Medical & biological engineering & computing 58 (2020): 1739-1749.

Yankelevitz, D. F et al. "Effect of radiation therapy on thoracic and lumbar bone marrow: evaluation with MR imaging." AJR. American journal of roentgenology 157.1 (1991): 87-92.

Extended European Search Report in related European Application No. 22856434.0 mailed on May 30, 2025, 9 pages.

Campos, Fernando O. et al. "Characterizing the clinical implementation of a novel activation-repolarization metric to identify targets for catheter ablation of ventricular tachycardias using computational models." Computers in Biology and Medicine 108 (2019): 263-275.

Rodriquez, K. (Authorized officer), International Search Report and Written Opinion in corresponding International Application No. PCT/US2022/039382 mailed on Aug. 4, 2022, 8pages.

Bi, Xiangpeng et al. "A Multi-Scale Computational Model for the Rat Ventricle: Construction, Parallelization, and Applications." Computer Methods and Programs in Biomedicine 208 (2021): 106289.

Child, Nicholas et al. "An activation-repolarization time metric to predict localized regions of high susceptibility to reentry." Heart rhythm 12.7 (2015): 1644-1653.

Orini, Michele et al. "Evaluation of the reentry vulnerability index to predict ventricular tachycardia circuits using high-density contact mapping." Heart Rhythm 17.4 (2020): 576-583.

Schmidt, Constanze et al. "Genetic Ablation of TASK-1 (Tandem of P Domains in a Weak Inward Rectifying K+ Channel-Related Acid-Sensitive K+ Channel-1)(K2P3. 1) K+ Channels Suppresses Atrial Fibrillation and Prevents Electrical Remodeling." Circulation: Arrhythmia and Electrophysiology 12.9 (2019): e007465.

Doherty, F. (Authorized officer), International Preliminary Report on Patentability in corresponding International Application No. PCT/US2022/039382 mailed on Feb. 22, 2024, 7 pages.

VENTRICULAR TACHYCARDIA ABLATION SITE IDENTIFICATION

CROSS-REFERENCE TO RELATED APPLICATIONS

This application is the national stage entry of International Patent Application No. PCT/US2022/039382, filed on Aug. 4, 2022, and published as WO 2023/018593 A1 on Feb. 16, 2023, which claims the benefit of U.S. Provisional Patent Application Ser. No. 63/231,466, filed Aug. 10, 2021, which are hereby incorporated by reference herein in their entireties.

FIELD

This disclosure relates generally to computer-aided identification of ablation sites to manage ventricular tachycardia.

BACKGROUND

In general, patients with structural heart disease are prone to develop reentrant ventricular tachycardia, which could lead to sudden cardiac death. Current therapeutic interventions are anti-arrhythmic drugs, implantable cardioverter-defibrillators, and radiofrequency catheter ablation. Anti-arrhythmic drugs can decrease the recurrence of arrhythmia, but may cause severe side-effects and are not effective in reducing mortality. Moreover, anti-arrhythmic drugs have a worse efficacy in protecting patients from sudden cardiac death in comparison to implantable cardiovascular defibrillators. While implantable cardioverter defibrillators may normalize cardiac rhythm as soon as the potentially lethal arrhythmia has occurred, they are often associated with inappropriate shocks, component malfunction, and other complications.

Radiofrequency catheter ablation by direct administration of radiofrequency energy to regions of conduction delay is an effective treatment that results in ventricular tachycardia termination and/or reduction of recurrent ventricular tachycardia. Radiofrequency catheter ablation has an overall success rate of 56-77% in patients with post-myocardial infarction ventricular tachycardias. Precise localization of the perpetrator regions in the heart is paramount in the effectiveness of radiofrequency catheter ablation treatment, however, it is difficult to achieve.

Currently, activation mapping of the tachycardia or electro-anatomical mapping during pacing is the clinical practice to identify myocardial regions to be targeted by ablation. These invasive procedures require multiple ventricular tachycardia inductions that are potentially hazardous to patients. Also, ventricular tachycardia induction may not be possible in sedated patients. If the ventricular tachycardia is inducible, the ventricular tachycardia may be short-lasting or hemodynamically not tolerated. Thus, accurate identification of the regions where re-entrant arrhythmias perpetuate by non-invasive techniques is desirable.

The reentry vulnerability index (RVI) provides a directional quantitative activation-repolarization metric relative to two points that can be used to detect potential entry and exit sites of a re-entrant arrhythmia during one paced rhythm. The reentry vulnerability index is determined based on the spatial relation between activation and repolarization times of a premature beat.

Gene therapy may facilitate non-destructive treatment replacing or supplementing present therapeutic approaches such as radiofrequency catheter ablation. Gene therapy has been shown to be safe and effective in animal models post-myocardial infarction.

BRIEF DESCRIPTION OF THE DRAWINGS

Various features of the embodiments can be more fully appreciated, as the same become better understood with reference to the following detailed description of the embodiments when considered in connection with the accompanying figures, in which.

DESCRIPTION OF THE EMBODIMENTS

Figure 1:
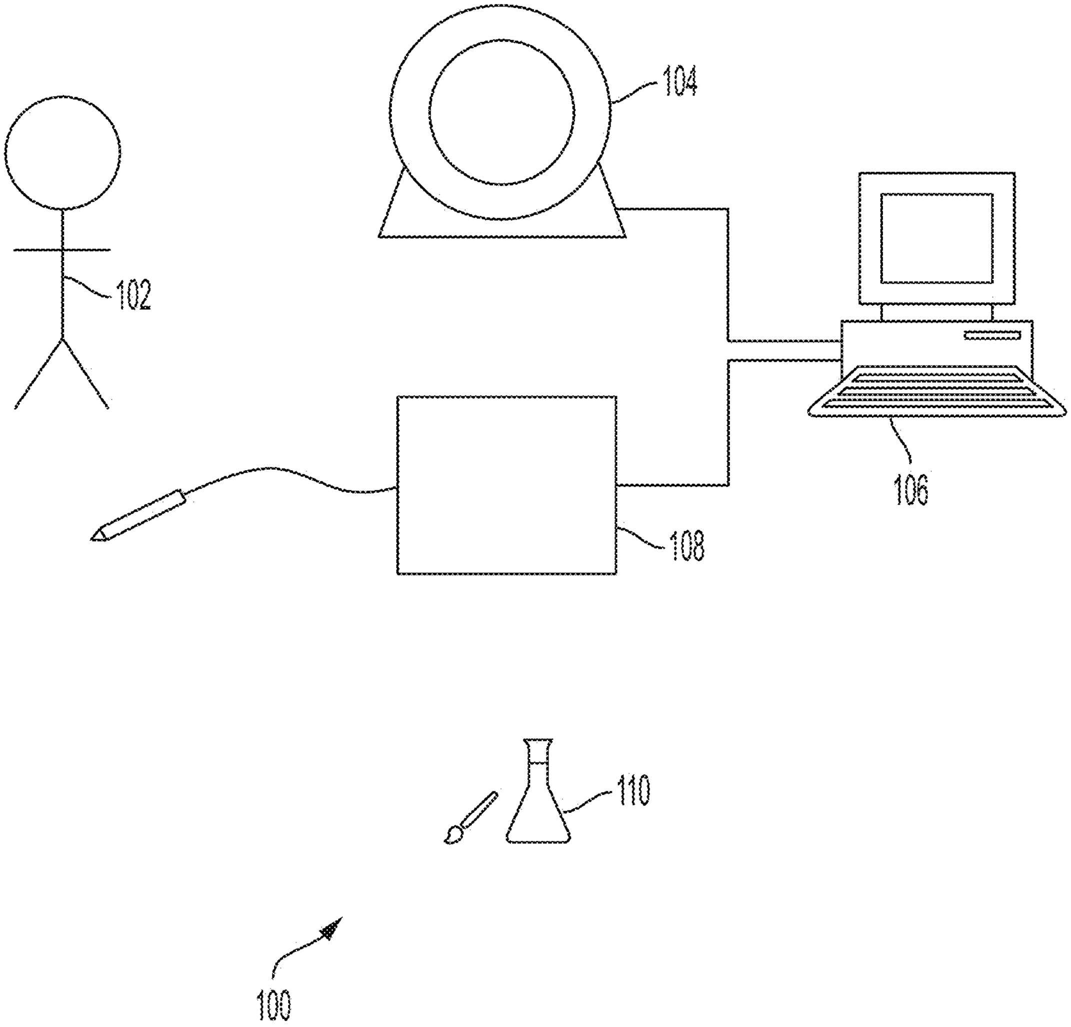
FIG. 1 is a schematic diagram of a system for identifying a ventricular tachycardia ablation site according to various embodiments.

Reference will now be made in detail to example implementations, illustrated in the accompanying drawings. Wherever possible, the same reference numbers will be used throughout the drawings to refer to the same or like parts. In the following description, reference is made to the accompanying drawings that form a part thereof, and in which is shown by way of illustration specific exemplary embodiments in which the invention may be practiced. These embodiments are described in sufficient detail to enable those skilled in the art to practice the invention and it is to be understood that other embodiments may be utilized and that changes may be made without departing from the scope of the invention. The following description is, therefore, merely exemplary.

Life threatening ventricular tachycardia is often a precursor to sudden cardiac death. Ventricular tachycardia may occur in patients with weakened heart muscle (myocardiopathy) and/or chronic myocardial infarction. Radiofrequency catheter ablation at regions of conduction delay is the standard treatment to prevent the recurrence of these arrhythmias. However, the ventricular-tachycardia induction that is required in this procedure is not always possible in patients with hemodynamic instability. Further, substrate changing may occur under anesthesia, which hampers accurate localization of reentry. Moreover, there may be more than one potential site of reentry, thus several ventricular-tachycardia inductions may be required, which may be difficult for the patient.

Some embodiments solve the aforementioned problems and identify one or more ventricular tachycardia ablation sites non-invasively, without requiring ventricular-tachycardia induction in the patient. Some embodiments utilize a reentry susceptibility map on a personalized 3D left ventricular image-based computer-implemented model to identify such ablation sites. More particularly, some embodiments simulate a premature heartbeat or ventricular tachycardia in the model to gather data used to identify such ablation sites in the patient. Further, some embodiments validate the identified ablation sites by simulating ablation and then attempting to simulate induction of a premature heartbeat or ventricular tachycardia in the model. If the simulated induction is unsuccessful at producing simulated ventricular tachycardia or a premature heartbeat, then the identified ablation site is likely correct.

This disclosure further presents a study of five patients (mean age 67.2±11.7 years, two female, three male) with post myocardial infarction ventricular tachycardia. Each patient underwent pre-ablation cardiac late gadolinium enhanced magnetic resonance imaging and subsequent clinical catheter radiofrequency ablation. Personalized reentry susceptibility maps were produced for the patients, and candidate ablation sites were identified according to various embodiments. Simulated ablations were performed to confirm effectiveness. Further, the identified ablation sites were compared with the patients' clinical ablation sites, which were identified using traditional invasive prior art techniques. Results of this study, which provide proof of the utility of embodiments, are presented herein.

Thus, some embodiments provide novel, non-invasive techniques that use reentry susceptibility maps overlayed on patient-specific 3D computational models to enhance the guidance of clinical ablation, e.g., catheter radiofrequency ablation.

FIG. 1 is a schematic diagram of a system 100 for identifying a ventricular tachycardia ablation site according to various embodiments. System 100 may be used to identify such an ablation site in patient 102, who may have ventricular tachycardia, e.g., due to a history of myocardial infarction. System 100 may further be used to ablate the identified site in patient 102 to correct the ventricular tachycardia.

Thus, system 100 includes catheter ablation device 108. Catheter ablation device 108 may be communicatively coupled to computer 106, to a different computer, or may be a standalone device. Catheter ablation device 108 may utilize radiofrequency energy to scar cardiac tissue to prevent or reduce electrical signals from passing using known techniques. Alternately, catheter ablation device 108 may use a different technique to produce scarring, such as cold temperatures, e.g., cryoablation.

System 100 may further, or alternatively, include genetic ablation material 110 for ablation based on localized gene modification. Localized gene modification may be accomplished by conveying genetic ablation material 110 to the ablation site using known techniques.

System 100 also includes magnetic resonance imaging device (MRI) 104. MRI 104 is communicatively coupled to computer 106, e.g., directly or by way of a computer network such as the internet. MRI 104 may be used to obtain tissue characterization of the myocardium of patient 102. More particularly, MRI 104 may be used with a gadolinium-based contrast agent to identify different regions of cardiac tissue, e.g., undamaged tissue versus scar tissue.

Figure 2:
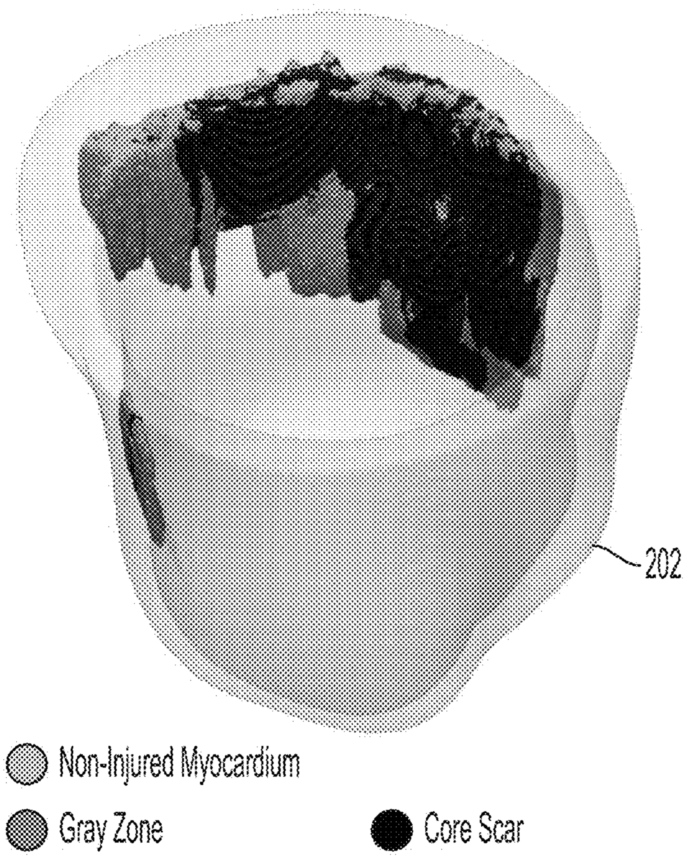
FIG. 2 depicts a segmented left ventricular fibrotic model according to various embodiments.

Computer 106 may generate and store an electroanatomical geometric model of the left ventricle of patient 102 based on late gadolinium enhanced MRI data produced by MRI 104 from patient 102. The model may be as shown and described in U.S. Pat. No. 10,765,336, entitled "System and Method for Planning a Patient-Specific Cardiac Procedure," which is hereby incorporated by reference in its entirety. The model may be constructed as follows, by way of non-limiting example. Computer 106 may segment the left ventricle, using a semi-automatic approach, into regions of non-infarcted tissue, gray zone, and core scar. Computer 106 may do so by applying signal intensity thresholding to the late gadolinium enhanced MRI data. An example segmented left ventricle depiction is shown in FIG. 2. Computer 106 may construct the model using virtual tetrahedral meshes (e.g., mean edge length, 396±110 μm) directly from the image segmentation with fiber orientations subsequently assigned using a validated rule-based technique. Each tetrahedron vertex may be referred to as a "node" herein. Computer 206 may identically assign electrophysiological parameters, e.g., action potential kinetics and conduction velocities, to the model. Computer 106 may assign standard human ventricular action potential kinetics and clinically measured conduction velocities to regions of non-infarcted tissue and gray zone in the model. The gray zone areas, which may have remodeled ionic current properties and impaired conduction, may be identified as having intensity intermediate to that of the non-infarcted and scar tissue in the late gadolinium enhanced MRI data. The core scar may be considered electrically inexcitable in the model. Simulation of electrical activity in the finite element heart models may be performed in the model in a monodomain representation of the myocardium, e.g., using the software Cardiac Arrhythmia Research Package (CARP).

Figure 5:
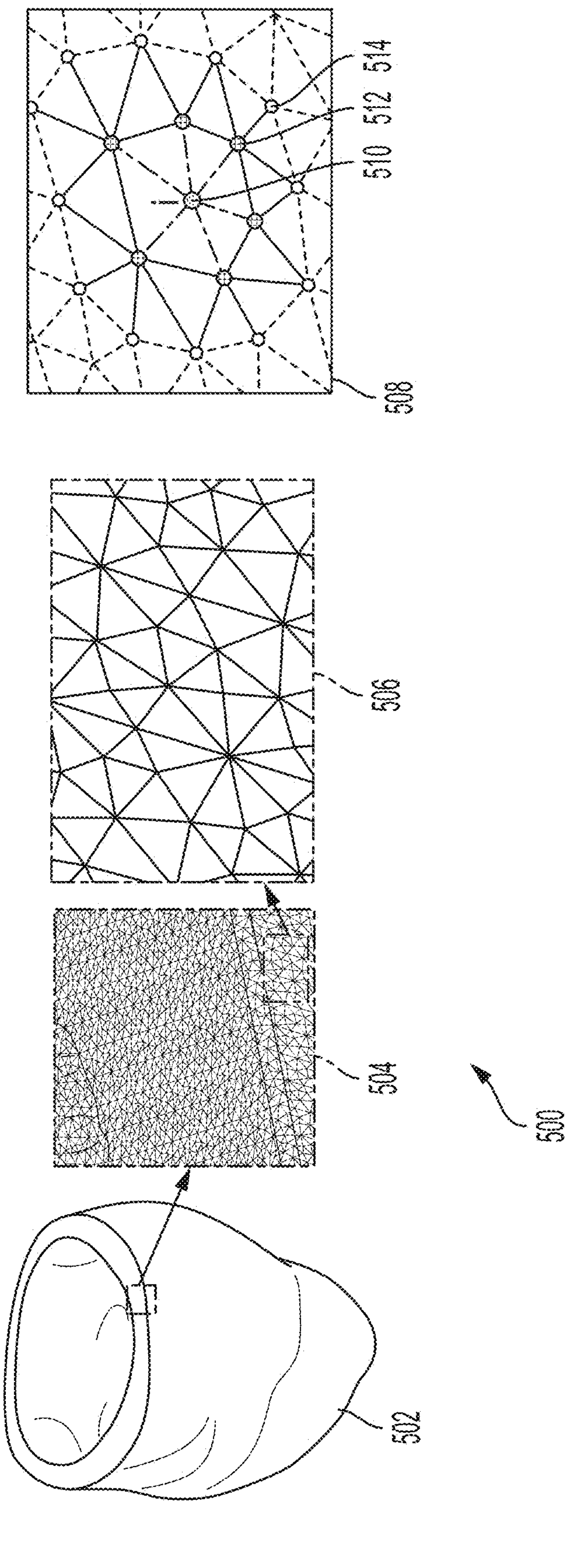
FIG. 5 presents diagrams depicting an example neighborhood about a node in an electroanatomical model of a left ventricle according to various embodiments.

Computer 106 may be further configured to generate and store a reentry susceptibility map based on the model, introduced presently and described in detail elsewhere herein, e.g., in reference to FIG. 5. The reentry susceptibility map may be based on a simulated pacing protocol applied to the model. More particularly, the reentry susceptibility map may be derived from data produced by the model after simulated induction of a single premature heartbeat or ventricular tachycardia in the model by way of a simulated rapid pacing protocol. Such data may include activation times and repolarization times at each of a plurality of nodes (e.g., all nodes) resulting from the simulated rapid pacing protocol. Thus, the reentry susceptibility map may be based on a plurality of activation and repolarization times produced by the model using a rapid pacing protocol.

The rapid pacing protocol may utilize multiple pacing locations evenly distributed in the model. In the study of five patients, seven pacing locations were used: three basal, three mid-myocardial, and one apical. The pacing locations may be projected to the nearest region of gray zone. The pacing protocol may include multiple steady state stimuli (these stimuli may be referred to as "S1" herein) followed by a premature stimuli (referred to as "S2" herein) at each pacing site. In the study of five patients discussed herein, S1 pacing at a cycle length of 600 ms was delivered for six beats to achieve a steady-state, followed by a premature stimulus S2 initially given at 300 ms. The S1-S2 timing may be progressively shortened from 300 ms until a premature heartbeat or ventricular tachycardia reentry is induced. If reentry cannot be induced with the first premature stimulus, determined by electrical quiescence, additional successive premature stimuli (S3, S4, S5) may be delivered at 250 ms after the previous stimulus, until ventricular tachycardia is induced. Sustained reentry may be simulated in the model for five seconds, for example. For each ventricular tachycardia morphology induced in the model, the reentrant circuit may identified through visual analysis of the 3D reentrant wave propagation depicted in the model. If reentry does not occur following S5, the model heart may be considered non-inducible from that pacing site.

Computer 106 may compute and record the activation times and repolarization times produced by the simulated ventricular tachycardia induced by the rapid pacing protocol. More particularly, the time-series transmembrane potential may be recorded for a plurality of nodes (e.g., every node) in the model for the duration of each simulated rapid pacing and ventricular tachycardia at each pacing location. For each pacing location, a time of activation (e.g., a time of maximum derivative of the simulated transmembrane potential, dV/dt) and a time of repolarization (e.g., a time of a −70 mV crossing) following the shortest S2 stimulus may be determined for a plurality of nodes (e.g., every node) in the model. Computer 106 may extract and store surface meshes, containing the S2 activation and repolarization times, for each reentry-inducing pacing site. The meshes may be based on (e.g., overlayed on) the tetrahedral meshes of the model. The activation and repolarization time data may be subsequently used to generate a reentry susceptibility map as described further herein, e.g., in reference to FIG. 4.

FIG. 2 depicts a segmented left ventricular fibrotic model 202 according to various embodiments. Segmented left ventricle model 202 was generated from late gadolinium enhanced MRI data, thresholded for intensity. Thus, segmented left ventricle 202 shows regions of normal, non-injured tissue, gray zone tissue, and scar tissue. The 3D segmentation data may be stored in computer 104 of FIG. 2.

Figure 3:
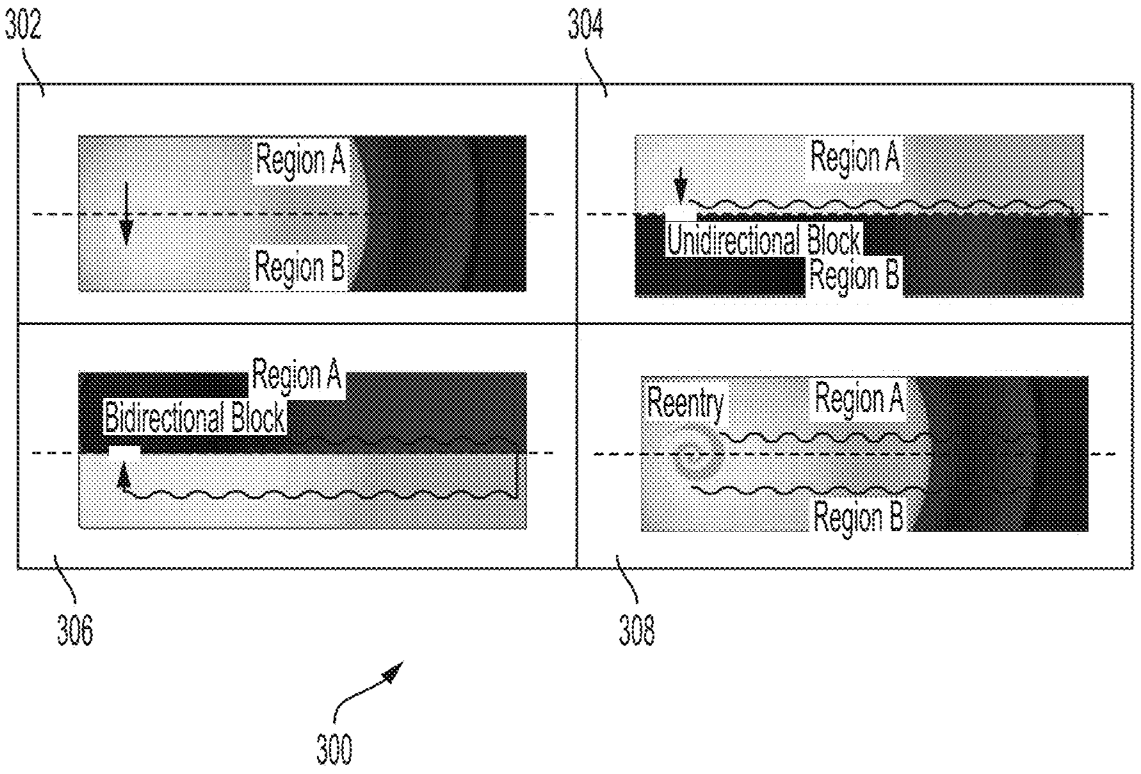
FIG. 3 presents schematic diagrams depicting various states of premature activation wavefronts according to various embodiments.

FIG. 3 presents schematic diagrams 300 depicting various states of premature activation wavefront according to various embodiments. In particular, diagrams 300 depict various states of premature activation wavefront after the rapid pacing protocol's S1-S2 stimulation. In charts 300, activation wavefronts are represented by black arrows. Normal propagation chart 300 shows that, following a rapid pacing protocol that utilizes signals S1 and S2, a premature activation wavefront (S2) travels from a proximal region ("Region A" in charts 300) to a distal region ("Region B" in charts 300). In the presence of damaged myocardium, the rapid pacing protocol may result in any one of three states based on the excitability of the surrounding myocardial cells. If the Region B has not yet regained excitability at the time of arrival of S2, the wavefront cannot enter Region B. This results in a unidirectional block, as depicted in unidirectional block chart 302. Hence, as shown in unidirectional block chart 302, the wavefront navigates along the border between the two regions to an excitable area to enter. The wavefront may continue its propagation in the distal region and may return to the proximal zone. If the proximal region has not yet regained excitability, the wavefront terminates, as depicted in bidirectional block chart 306. However, if the proximal zone is excitable, the wavefront progresses back to the proximal region and proceeds to oscillate between the two regions, as shown in reentry chart 308. That is, the activation wavefront periodically reenters both regions because both regions become re-excitable in a bi-phasic manner, resulting in reentry and ventricular tachycardia.

Figure 4:
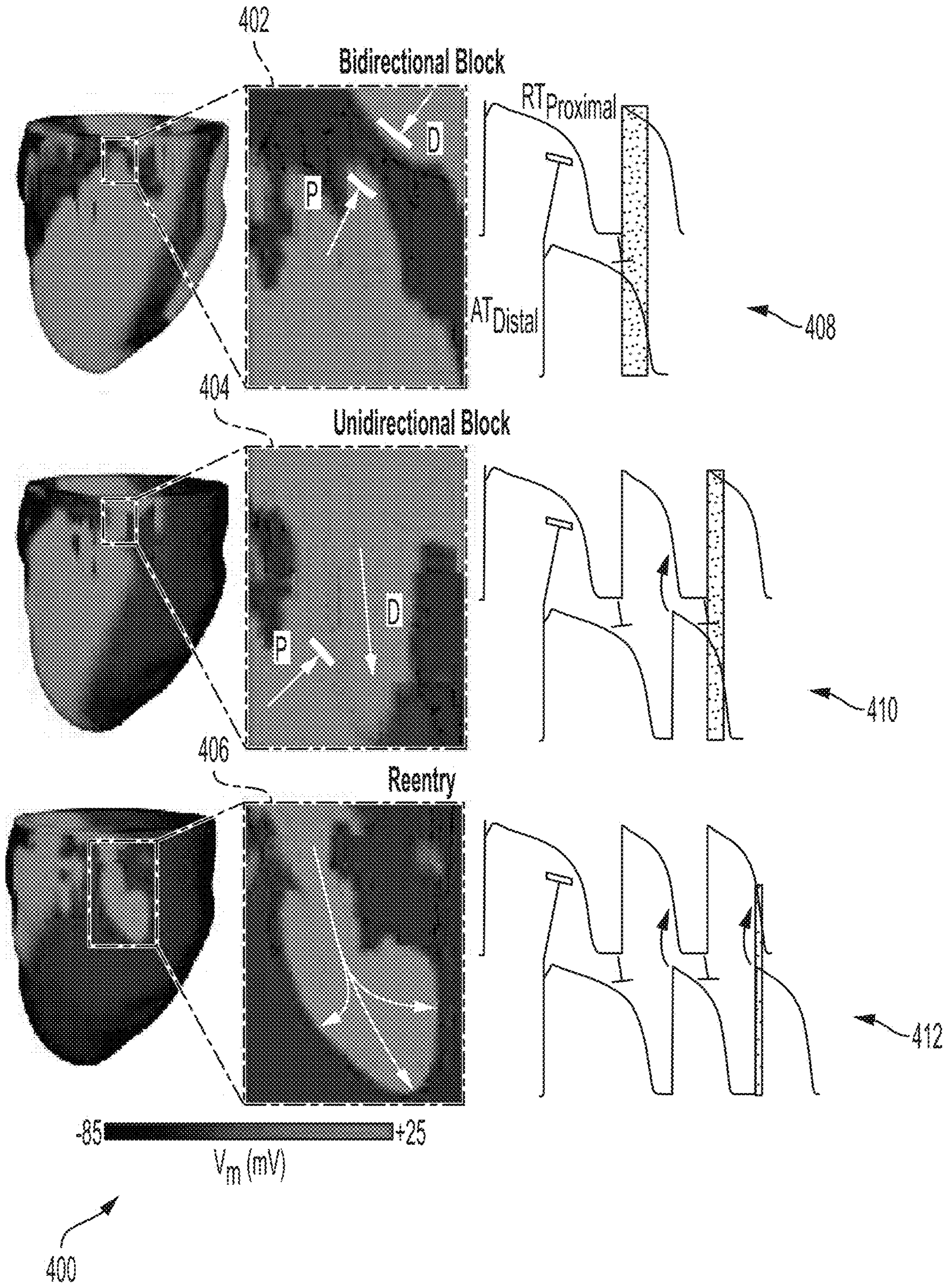
FIG. 4 presents diagrams depicting bidirectional wavefront block, unidirectional wavefront block, and wavefront reentry, as well as their respective action potential tracings, according to various embodiments.

FIG. 4 presents diagrams depicting bidirectional wavefront block 402, unidirectional wavefront block 404, and wavefront reentry 406, as well as corresponding action potential tracings 408, 410, 412, according to various embodiments. The labels "P" and "D" represent proximal and distal regions, respectively, and the arrows represent wavefronts. According to bidirectional wavefront block 402, the proximal and distal wavefronts collide following the S1 stimulus and no further activation occurs. According to unidirectional block 404, the proximal wavefront encounters an inexcitable region following the premature S2 stimulus and does not propagate. The distal wavefront arrives and propagates through the now excitable tissue. According to wavefront reentry 406, the distal wavefront continues to propagate through excitable tissue for multiple cycles without any additional stimulus.

Action potential tracings 408, 410, 412 show repolarization curves for the proximal regions and activation time curves for the distal regions. The widths of the bands between the repolarization times and the activation times provide indications of reentry susceptibility due to wavefronts travelling from the proximal regions to the distal regions. In particular, the narrower the band, the more susceptible the region is to reentry due to the particular wavefront travelling from the proximal to the distal regions.

The width of the bands may be quantified according to various embodiments toward producing a reentry susceptibility map. More particularly, using the recorded repolarization and activation times obtained from the simulated pacing in the model, some embodiments calculate one or more a directional quantitative activation-repolarization metrics, e.g., in the form of reentry vulnerability indices. Such a directional quantitative activation-repolarization metric indicates reentry susceptibility due to wavefronts travelling between the respective proximal and distal region.

In the present context, following a premature S1-S2 stimulus, the directional quantitative activation-repolarization metric relative to two points may be in the form of a time interval duration, which determines the spatial relationship between the S2 following/succeeding repolarization time and the S2 distal activation time. Hence, some embodiments calculate the directional quantitative activation-repolarization metrics between each proximal node i and distal node j (activated later than i) using the surface meshes containing the S2 activation and repolarization times recorded as described above in reference to FIG. 1. These directional metrics may subsequently be used to generate a reentry susceptibility localization map according to various embodiments.

Thus, the directional quantitative activation-repolarization metric provides a quantitative measure of the activation-repolarization time interval, which predicts whether a premature activation wavefront is capable of inducing reentry. An example non-limiting definition of a directional quantitative activation-repolarization metric is presented here. For two nodes i and j in a mesh of the myocardial surface for which the activation time due to the S2 beat initiated at node p is later in node j than i, the directional quantitative activation-repolarization metric value between i and j due to pacing at node p is denoted herein as $DQAPM_{i,j,p}$ and may be defined as, by way of non-limiting example:

$$DQAPM_{i,j,p} = RT_{i,p} - AT_{j,p} \quad (1)$$

In Equation (1), $RT_{i,p}$ represents the repolarization time of node i due to pacing at node p, and $AT_{,pj}$ represents the activation time of node j due to pacing at node p. Defined this way, the directional quantitative activation-repolarization metric is a metric between two nodes relative to a direction of wavefront propagation.

In order to express the vulnerability at a particular node i irrespective of choice of distal node, the reentry susceptibility localization map value at a node i may be defined as an average of directional quantitative activation-repolarization metrics $DQAPM_{i,j,p}$ over all pacing sites and over all nodes j that are neighboring nodes to i for which $AT_j > AT_i$:

$$QAPM_i = \frac{\sum_{i=1,\ldots,N_j,p\in P}(RT_{i,p} - AT_{j,p})}{N_j} \quad (2)$$

In Equation (2), the term P represents the set of pacing nodes, and the term $N_j$ represents the number of neighboring nodes to j that are distal to node i. The neighboring nodes j to a particular node i may be defined in various ways according to various embodiments. According to some embodiments, the neighboring nodes j to a node i are defined as the nodes that are within a specified distance, e.g., 1 mm, to i. According to some embodiments, the neighboring nodes j to a node i are defined as the nodes that are first or second order neighbors to i, as described presently in reference to FIG. 5. In general, values for Equation (2) at particular nodes may be calculated using the surface meshes containing the S2 activation and repolarization times recorded as described above in reference to FIG. 1. Thus, Equation (2) may be used to construct a surface mesh with a reentry susceptibility quantification value at each node. Such a mesh may be referred to herein as a reentry susceptibility localization map.

FIG. 5 presents diagrams 500 depicting an example neighborhood about a node i 510 in an electroanatomical model 502 of a left ventricle according to various embodiments. The anatomical model 502 may utilize a mesh 504 composed of tetrahedrons as described above in reference to FIG. 1. The surface of such a tetrahedral mesh 504 may be composed of triangles 506, where the vertices of the triangles 506 form nodes. For a given node i 510, the first order neighbors, e.g., first order neighbor 512, may be defined as the nodes that are directly connected to i 510 by an edge of a tetrahedron. For the given node i 510, the second order neighbors, e.g., second order neighbor 514, may be defined as the nodes that are directly connected to a first order neighbor of i 510. According to some embodiments, the neighborhood of a node i, for purposes of calculating a reentry susceptibility localization map value at i, consists of the first and second order neighbors of i. According to some embodiments, additional higher order neighbors may be included. According to some embodiments, only first order neighbors are included. A nearest neighbor or shortest path algorithm may be employed to determine neighborhoods for nodes according to various embodiments. A shortest path algorithm may facilitate neighborhood localization in both homogenous and inhomogeneous surface mesh models and is a computationally fast approach for large data sets.

Returning to the discussion of the study of five patients, when a pacing site resulted in reentry, a reentry susceptibility localization map was constructed from the S2 activation and repolarization times preceding the reentry. Each patient's reentry susceptibility localization map was used to choose the virtual ablation locations in the patient-specific models. To account for multiple locations of reentry susceptibility, the study virtually ablated up to three nodes with the lowest reentry susceptibility quantification values from each reentry susceptibility localization map for each patient. Due to the high resolution of the surface data, multiple nodes in close proximity were often classified as one highly vulnerable node. If two ablation locations were within 3 mm of each other, the study only performed one ablation to account for clinical reentry susceptibility quantification diameters and included the node with the next lowest reentry susceptibility quantification value for virtual ablation at a cluster of nodes. The virtual lesions were treated as non-conducting tissue and the diameter of the spherical ablations were performed at 3, 5, 7, and 10 mm to account for myocardial wall thickness and heterogeneous fibrotic remodeling. The virtually ablated heart models were then subjected to the rapid pacing protocol described herein and, if reentry did not occur, the ablation was deemed successful. If the virtual ablations with a diameter of 10 mm did not terminate the reentry, virtual ablations were performed by including the second RVI node at 10 mm (and then again including the third at 10 mm if necessary) in the same fashion and subjected to the rapid pacing protocol. If the virtual ablations were successful, the study decreased the diameters to 7, 5, and 3 mm of the virtual ablations until the reentry was not terminated.

Figure 6:
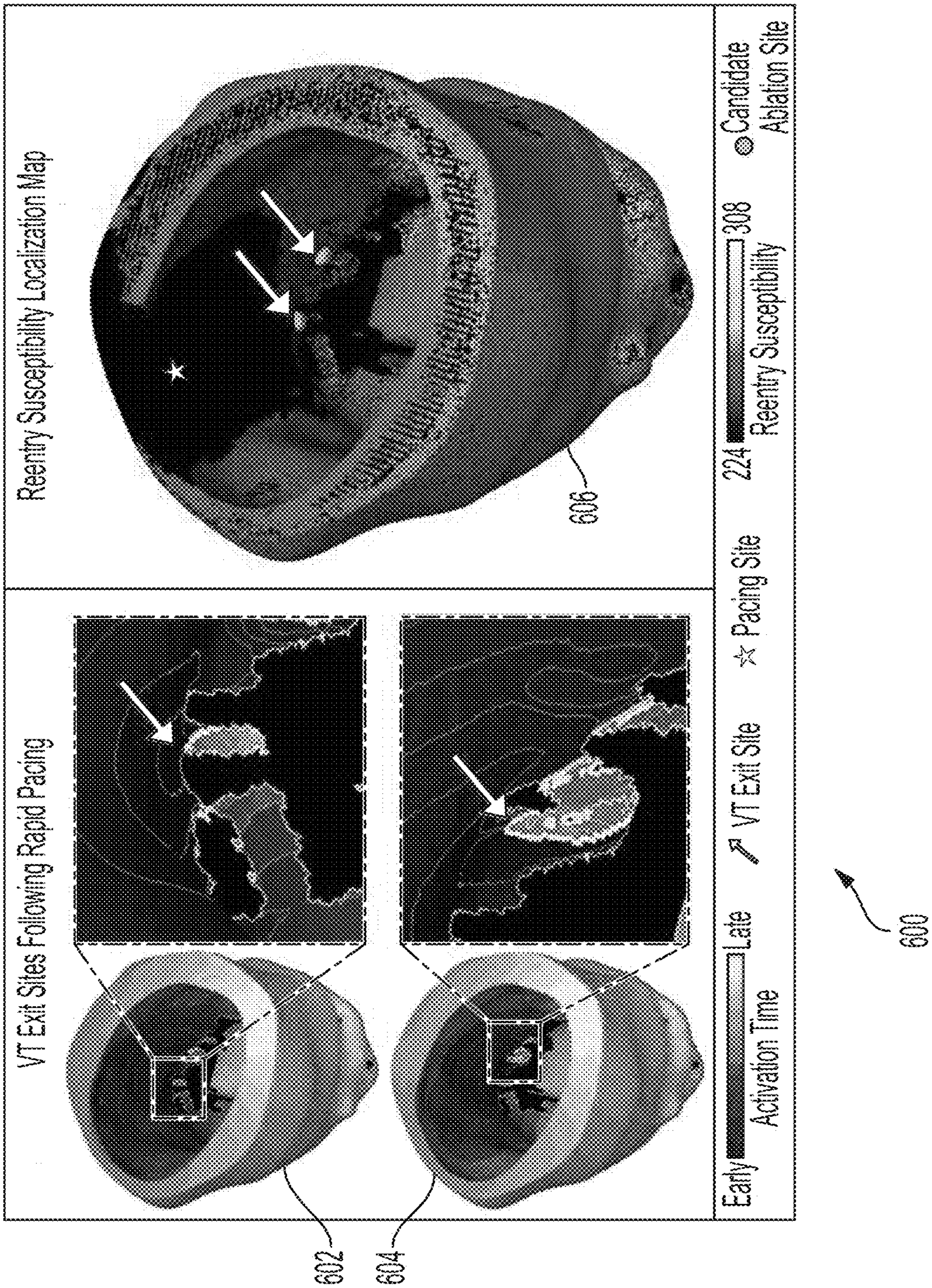
FIG. 6 presents diagrams relevant to determining locations for ablation for a specific patient according to various embodiments.

FIG. 6 presents diagrams 600 relevant to determining locations for ablation in Patient 4 from the study of five patients according to various embodiments. In particular, FIG. 6 includes diagram 602 showing a ventricular tachycardia exit site (arrow) for Patient 4 following rapid pacing at the basal anteroseptal wall following S3 pacing. Diagram 604 shows showing a ventricular tachycardia exit site (arrow) for Patient 4 following rapid pacing at the basal anteroseptal wall for the next cycle of reentry. Diagram 606 shows a reentry susceptibility localization map calculated following S2 pacing. Locations of the lowest reentry susceptibility values, which are candidates for ablation, are indicated by arrows.

The rapid pacing protocol induced eleven sustained ventricular tachycardia events across the five patients, with nine of the sustained ventricular tachycardia events being unique. Reentry susceptibility values were calculated for all surface nodes that sustained simulated electrical activity (non-injured myocardium and GZ) in each patient using S2 activation and repolarization data. FIG. 6 depicts two examples of ventricular tachycardia exit sites (602, 604, see arrows) in Patient 4 following rapid pacing at the basal anteroseptal wall. The exit sites shown were identified with the first (top) and fourth (bottom) nodes of the lowest reentry susceptibility values. Reentry susceptibility localization maps were calculated for the five patient-specific models contained an average of 459,037±115,343 [316122-588120] nodes. The ventricular tachycardia exit sites were correctly identified among the top 10 [1-10] nodes with the lowest reentry susceptibility values for each inducible pacing site of the five virtual heart models. Additionally, in patients with more than one inducible pacing location, the ventricular tachycardia exit sites could be identified by using the reentry susceptibility localization map from a single pacing location (Patient 1 and Patient 4) using the top fifteen nodes with the lowest reentry susceptibility values.

Figure 7:
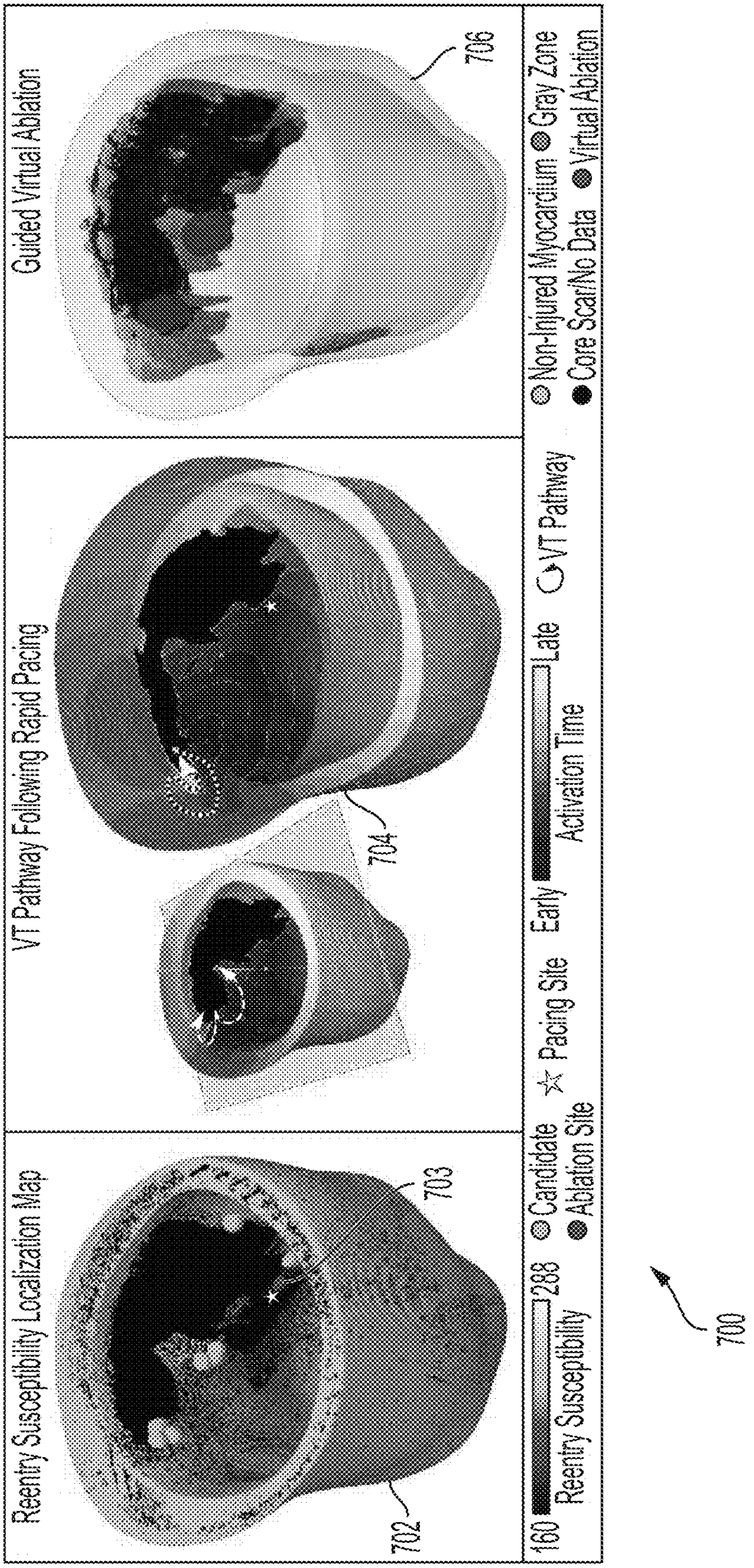
FIG. 7 presents diagrams relevant to determining locations for ablation in a specific patient according to various embodiments.

FIG. 7 presents diagrams 700 relevant to determining locations for ablation in Patient 6 from the study of five patients according to various embodiments. Diagram 702 depicts a reentry susceptibility localization map 702 for Patient 6 generated from S2 pacing data with the fifteen lowest reentry susceptibility values highlighted. Candidate ablation location 703 was excluded due to close proximity to the pacing site (mid anteroseptal wall). Diagram 704 depicts ventricular tachycardia pathway (arrow). Diagram 706 depicts that virtual ablation for the five lowest value reentry susceptibility locations nodes terminated the ventricular tachycardia using the follow-up pacing protocol.

The ventricular tachycardia exit site in Patient 6 occurs in the basal region of fibrotic remodeling (see 704) and the lowest reentry susceptibility value in the respective cluster is first identified by the second lowest reentry susceptibility value in the reentry susceptibility localization map. Virtual ablation at the first location at 10 mm was unsuccessful, as the ablation did not overlap the exit site. Virtual ablation (4 mm) of the lowest 5, 10, and 15 sites successfully terminated the ventricular tachycardia following rapid pacing. Diagram 706 depicts virtual ablation of the five lowest-valued locations. The virtual ablation resulted in 1.49% of additional non-conducting tissue.

The study of five patients compared the ablation locations determined according to the reentry susceptibility localization map with the ablation locations determined using clinical invasive prior art techniques. That is, the study of five patients evaluated the efficacy and efficiency of the virtual ablations determined according to the reentry susceptibility localization map approach of various embodiments. Virtual ablations were deemed successful if the ventricular tachycardia could not be induced by the rapid pacing protocol. The study compared the fraction of total heart surface and location of each patient's virtual ablations to the clinical lesions. The virtual ablation fraction was calculated using the number of tetrahedra in each ablation of the left ventricular meshes as compared with the total number of tetrahedra in the mesh. The location of the virtual ablations was visually compared to that of the clinical lesions using the same anatomical orientation. Table 1 below depicts parameters relating to the clinical ablations.

TABLE 1

| Patient | Gender | Age | Number of Clinical Ablation Sites | Left Ventricular Volume (mL) | Clinical Ablation Volume (mL) | Clinical Ablation Fraction (%) |
|---|---|---|---|---|---|---|
| 1 | Male | 67 | 356 | 147.02 | 5.68 | 3.87 |
| 2 | Female | 53 | 174 | 90.97 | 3.06 | 3.36 |
| 3 | Male | 85 | 296 | 135.74 | 5.97 | 4.4 |
| 4 | Male | 69 | 128 | 144.38 | 6.93 | 4.8 |
| 5 | Female | 62 | 234 | 63.72 | 2.77 | 4.35 |

Properties of the reentry susceptibility localization maps and the virtual ablation results are summarized in Table 2 below. The overall sensitivity and specificity of using the reentry susceptibility localization map to identify susceptible regions to reentry followed by guided virtual ablation was 100%.

TABLE 2

| Patient | Total No. surface nodes | Inducible pacing location | No. Premature Stimuli | No. of RVI clusters (RVI Rank) | Smallest ablation diameter (mm) | Virtual Ablation Fraction | Virtual ablation guided by the RVI |
|---|---|---|---|---|---|---|---|
| 1 | 588120 | Mid lateral | S5 | 1 (Lowest) | 11 | 1.86 | Successful |
| | | Basal inferoseptal | S4 | 1 (Lowest) | 5 | 0.42 | Successful |
| | | Basal inferior | S5 | 1 (Lowest) | 9 | 1.64 | Successful |
| 2 | 370440 | Basal inferior | S5 | 1 ($2^{nd}$ Lowest) | 7 | 0.82 | Successful |
| | | Apex | S5 | 2 ($2^{nd}$ Lowest) | 7 | 0.81 | Successful |
| 3 | 471302 | Basal anteroseptal | S3 | 1 (Lowest) | 6 | 0.54 | Successful |
| | | Mid anteroseptal | S3 | 1 (Lowest) | 6 | 0.34 | Successful |
| 4 | 549200 | Mid lateral | S3 | 2 ($2^{nd}$ Lowest) | 6 | 0.39* | Successful |
| | | Mid inferior | S3 | 1 (Lowest) | 10 | 2.80 | Successful |
| | | Apex | S3 | 2 ($2^{nd}$ Lowest) | 10 | * | Successful |
| 5 | 316122 | Mid anteroseptal | S3 | 1 (Lowest) | 5 | 1.00 | Successful |

Figure 8:
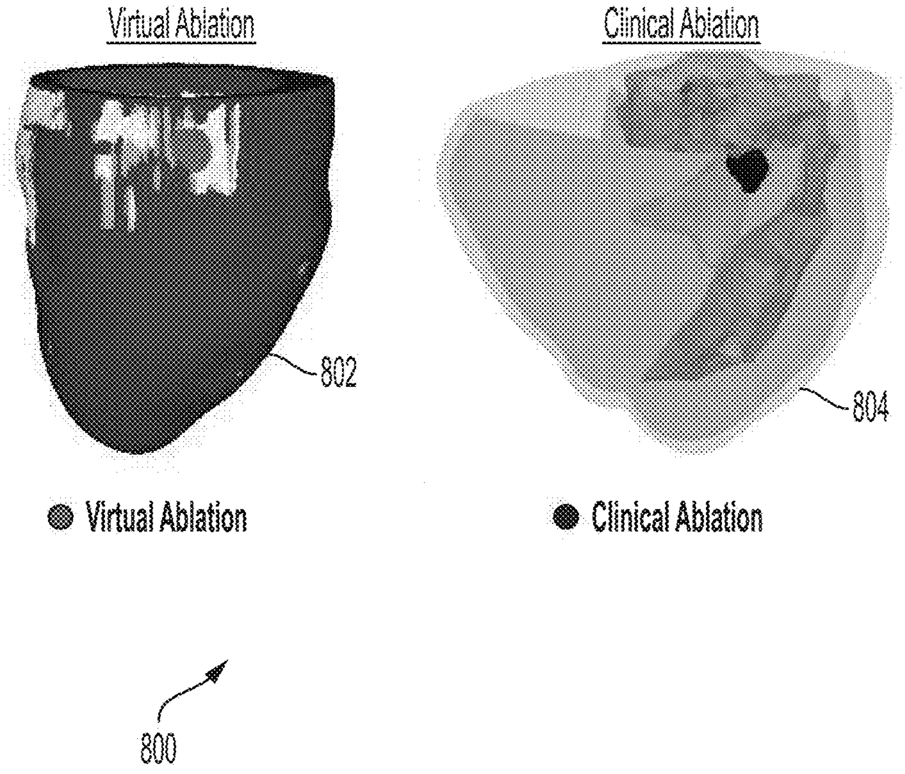
FIG. 8 presents diagrams depicting, for a specific patient, a virtual ablation map and a clinical ablation map, according to various embodiments.

FIG. 8 presents diagrams depicting, for Patient 1 from the study of five patients, virtual ablation map 802 and clinical ablation map 804, according to various embodiments. For comparison, FIG. 2, described above, depicts a fibrotic remodeling map for Patient 1, and FIG. 6 depicts an activation map following a pacing protocol, an activation times map, a repolarization times map, and a reentry susceptibility localization map for Patient 1. Virtual ablation map 802 shows a location of virtual ablation, based on the location of lowest values of the reentry susceptibility localization map (e.g., reentry susceptibility localization map 608 of FIG. 6) for Patient 1. Clinical ablation map 804 depicts the location of the actual clinical ablation for Patient 1 as determined using invasive prior art techniques. In particular, clinical ablation map 804 shows the location of clinical ablation projected onto the virtual heart model for Patient 1. Visual inspection shows that the location and size of the ablation is comparable between virtual ablation map 802 and clinical ablation map 804. Per Table 1, the clinical ablation fraction for Patient 1 is 3.87%, and per Table 2, the virtual ablation fraction for Patient 1 is comparable at 3.94%, spread across three locations.

Figure 9:
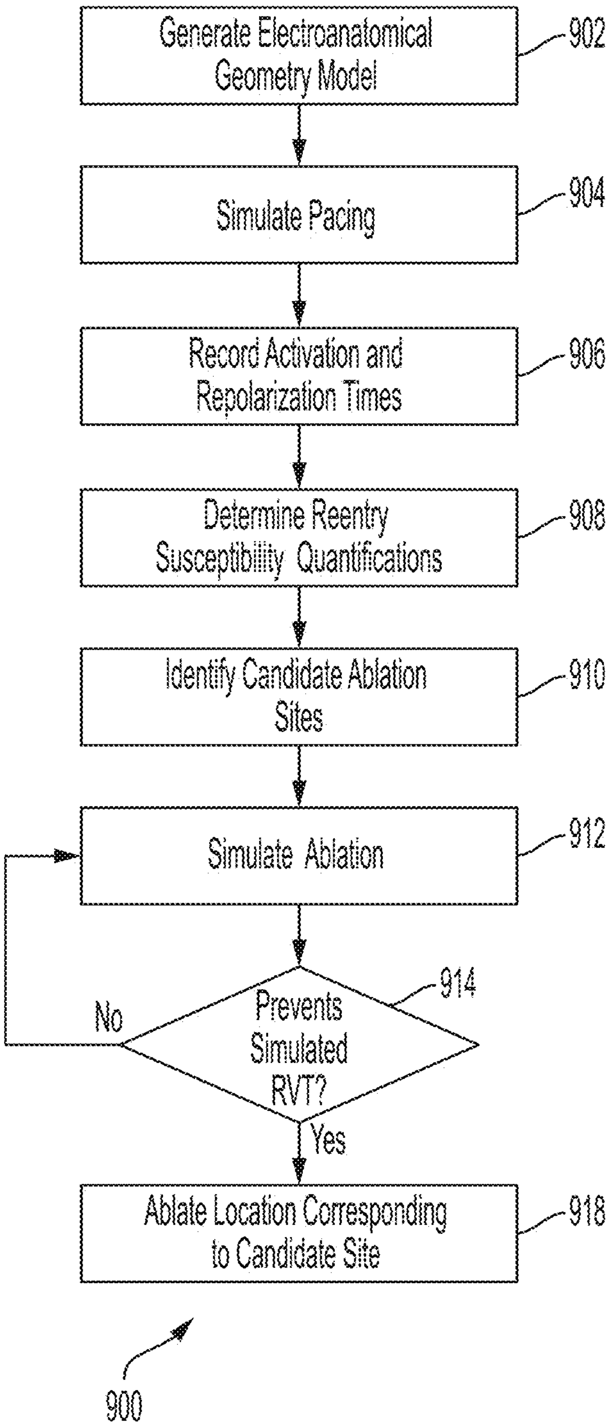
FIG. 9 is a flow chart depicting a method of identifying a ventricular tachycardia ablation site according to various embodiments.

FIG. 9 is a flow chart depicting a method 900 of identifying a ventricular tachycardia ablation site according to various embodiments. Method 900 may be implemented using system 100 as shown and described herein in reference to FIG. 2, for example. Method 900 may include techniques disclosed herein in reference to FIGS. 1-7.

At 902, method 900 includes generating an at least partial electroanatomical geometry model of a left ventricle of a patient. The actions of 902 may include generating an electroanatomical model as shown and described herein, e.g., in reference to FIGS. 1 and 2.

At 904, method 900 includes simulating pacing, in the model, in the left ventricle of the patient in order to induce a simulated single premature heartbeat in the model. The actions of 904 may include simulating pacing using a rapid pacing protocol, e.g., as shown and described herein in reference to FIG. 1

At 906, method 900 includes recording an activation time and a repolarization time resulting from the simulating pacing at each of a plurality of nodes in the model. The actions of 906 may include recording the activation times and repolarization times in a surface mesh of the model, e.g., as shown and described herein in reference to FIGS. 1-5.

At 908, method 900 includes determining, based on the plurality of activation times and repolarization times recorded per 906, a reentry susceptibility quantification at each of a plurality of nodes in the model. The actions of 908 may include generating a reentry susceptibility localization map, e.g., as shown and described herein in reference to FIGS. 4 and 5.

At 910, method 900 includes identifying a candidate ablation site based on the plurality of reentry susceptibility quantifications. For example, the candidate ablation site may include a location of minimal reentry susceptibility quantification value, e.g., as shown and described herein in reference to FIGS. 4-6.

At 912, method 900 includes simulating, in the model, an ablation at the candidate ablation site. The actions of 912 may be as described herein, e.g., in reference to FIG. 6.

At 914, method 900 determines whether the simulated ablation prevented a simulated rapid pacing protocol from inducing a simulated reentry ventricular tachycardia in the model. The actions of 914 may be as described herein, e.g., in reference to FIG. 6. If not, then control reverts to 912. If so, then control passes to 918.

At 916, method 900 includes ablating a location in the patient's left ventricle corresponding to the candidate ablation site. Any of a variety of ablation techniques may be utilized, such as by way of non-limiting example, radiofrequency ablation, genetic ablation by localized gene modification, cryoablation, or cardiac radioablation, e.g., based on stereotactic ionizing radiation.

Note that, in general, embodiments are not limited to determining the directional quantitative activation-repolarization metrics, and hence the reentry susceptibility localization map values, based on activation and repolarization times generated by the model disclosed herein. Electrocardiographic imaging (ECGI) uses the body surface electrocardiograms and the patient's heart-torso geometry using either MRI or computed tomography (CT). The equivalent dipole layer (EDL) inverse model reconstructs endo-epicardial surface map of activation and repolarization times. The EDL model assumes the current source distribution within the heart is equivalent to a dipole layer at the surface of the myocardium. Accordingly, some embodiments may determine the directional quantitative activation-repolarization metrics, and hence the reentry susceptibility localization map values, based on the activation-repolarization times determined by the ECGI, facilitating a minimally invasive approach to identify the region(s) susceptible to reentry.

Certain embodiments can be performed using a computer program or set of programs. The computer programs can exist in a variety of forms both active and inactive. For example, the computer programs can exist as software program(s) comprised of program instructions in source code, object code, executable code or other formats; firmware program(s), or hardware description language (HDL) files. Any of the above can be embodied on a transitory or non-transitory computer readable medium, which include storage devices and signals, in compressed or uncompressed form. Exemplary computer readable storage devices include conventional computer system RAM (random access memory), ROM (read-only memory), EPROM (erasable, programmable ROM), EEPROM (electrically erasable, programmable ROM), and magnetic or optical disks or tapes.

While the invention has been described with reference to the exemplary embodiments thereof, those skilled in the art will be able to make various modifications to the described embodiments without departing from the true spirit and scope. The terms and descriptions used herein are set forth by way of illustration only and are not meant as limitations. In particular, although the method has been described by examples, the steps of the method can be performed in a different order than illustrated or simultaneously. Those skilled in the art will recognize that these and other variations are possible within the spirit and scope as defined in the following claims and their equivalents.

What is claimed is:

1. A method of identifying an ablation site, the method comprising:

generating a model of at least one ventricle of a patient;

simulating pacing, in the model, in the at least one ventricle of the patient, wherein the simulating pacing induces a simulated single premature heartbeat in the model;

recording an activation time and a repolarization time resulting from the simulating pacing at each of a plurality of nodes in the model, whereby a plurality of activation times and repolarization times for the simulated single premature heartbeat are recorded;

determining, based on the plurality of activation times and repolarization times, a reentry susceptibility quantification at each of a plurality of nodes in the model, wherein a plurality of reentry susceptibility quantifications for the simulated single premature heartbeat are determined;

identifying a candidate ablation site based on the plurality of reentry susceptibility quantifications for the simulated single premature heartbeat;

simulating, in the model, an ablation at the candidate ablation site;

determining, using the model, that the simulating the ablation prevents a simulated pacing from inducing simulated reentrant ventricular tachycardia; and ablating a location in the at least one ventricle of the patient corresponding to the candidate ablation site.

2. The method of claim 1, wherein the ablating the location in the at least one ventricle of the patient comprises genetically ablating.

3. The method of claim 1, wherein the determining the reentry susceptibility quantification at each of the plurality of nodes in the model comprises, for each of a plurality of first and second nodes, determining a respective difference between a respective repolarization time at a respective first node and a respective activation time at a respective second node.

4. The method of claim 3, wherein the determining the reentry susceptibility quantification at each of the plurality of nodes in the model further comprises determining, for each of a plurality of proximal nodes, an average of differences between a respective repolarization time at a respective proximal node and a respective activation time at each of a plurality of respective distal nodes present in a respective neighborhood about the respective proximal node.

5. The method of claim 4, wherein each respective neighborhood comprises first and second order neighbors of the respective proximal node.

6. The method of claim 1, wherein the simulating pacing comprises simulating a plurality of regularly spaced stimuli followed by simulating a premature stimulus.

7. The method of claim 1, wherein the generating the model further comprises segmenting a representation of the at least one ventricle of the patient into at least scar tissue and normal tissue.

8. The method of claim 1, wherein the at least one ventricle comprises a left ventricle.

9. The method of claim 1, wherein the generating the model comprises acquiring a late gadolinium Magnetic Resonance Imaging (MRI) scan of the at least one ventricle of the patient.

10. A system for identifying an ablation site, the system comprising an electronic processor and computer readable instructions that, when executed by the electronic processor, cause the electronic processor to perform operations comprising:

generating a model of at least one ventricle of a patient;

simulating pacing, in the model, in the at least one ventricle of the patient, wherein the simulating pacing induces a simulated single premature heartbeat in the model;

recording an activation time and a repolarization time resulting from the simulating pacing at each of a plurality of nodes in the model, whereby a plurality of activation times and repolarization times are recorded for the simulated single premature heartbeat;

determining, based on the plurality of activation times and repolarization times, a reentry susceptibility quantification at each of a plurality of nodes in the model, wherein a plurality of reentry susceptibility quantifications for the simulated single premature heartbeat is determined;

identifying a candidate ablation site based on the plurality of reentry susceptibility quantifications for the simulated single premature heartbeat;

simulating, in the model, an ablation at the candidate ablation site;

determining, using the model, that the simulating the ablation prevents a simulated pacing from inducing simulated reentrant ventricular tachycardia; and ablating a location in the at least one ventricle of the patient corresponding to the candidate ablation site.

11. The system of claim 10, wherein the ablating the location in the at least one ventricle of the patient comprises genetically ablating.

12. The system of claim 10, wherein the determining the reentry susceptibility quantification at each of the plurality of nodes in the model comprises, for each of a plurality of first and second nodes, determining a respective difference between a respective repolarization time at a respective first node and a respective activation time at a respective second node.

13. The system of claim 12, wherein the determining the reentry susceptibility quantification at each of the plurality of nodes in the model further comprises determining, for each of a plurality of proximal nodes, an average of differences between a respective repolarization time at a respective proximal node and a respective activation time at each of a plurality of respective distal nodes present in a respective neighborhood about the respective proximal node.

14. The system of claim 13, wherein each respective neighborhood comprises first and second order neighbors of the respective proximal node.

15. The system of claim 10, wherein the simulating pacing comprises simulating a plurality of regularly spaced stimuli followed by simulating a premature stimulus.

16. The system of claim 10, wherein the generating the model further comprises segmenting a representation of the at least one ventricle of the patient into at least scar tissue and normal tissue.

17. The system of claim 10, wherein the at least one ventricle comprises a left ventricle.

18. The system of claim 10, wherein the generating the model comprises acquiring a late gadolinium Magnetic Resonance Imaging (MRI) scan of the at least one ventricle of the patient.

19. The method of claim 1, wherein the ablating the location in the at least one ventricle of the patient comprises ablating using radiofrequency energy.

20. The system of claim 1, wherein the ablating the location in the at least one ventricle of the patient comprises ablating using radiofrequency energy.

* * * * *